United States Patent
Du et al.

(10) Patent No.: US 7,428,902 B2
(45) Date of Patent: Sep. 30, 2008

(54) HUMIDIFIER SYSTEM FOR ARTIFICIAL RESPIRATION

(75) Inventors: Hong-Lin Du, Irvine, CA (US); Norio Hachisu, Costa Mesa, CA (US)

(73) Assignee: Newport Medical Instruments, Inc., Costa Mesa, CA (US)

( * ) Notice: Subject to any disclaimer, the term of this patent is extended or adjusted under 35 U.S.C. 154(b) by 722 days.

(21) Appl. No.: 11/013,512

(22) Filed: Dec. 15, 2004

(65) Prior Publication Data

US 2006/0124127 A1 Jun. 15, 2006

(51) Int. Cl.
- A62B 18/08 (2006.01)
- A62B 23/02 (2006.01)
- A62B 7/00 (2006.01)
- A62B 7/10 (2006.01)
- A61M 15/00 (2006.01)
- A61M 16/00 (2006.01)
- F24J 3/00 (2006.01)
- F28F 13/12 (2006.01)
- F28F 19/00 (2006.01)

(52) U.S. Cl. .................. 128/204.17; 128/201.13; 128/204.13; 128/205.27; 128/200.24; 128/204.18; 128/205.28; 165/119

(58) Field of Classification Search ............ 128/201.13, 128/204.13, 204.17, 205.27, 205.28; 165/119
See application file for complete search history.

(56) References Cited

U.S. PATENT DOCUMENTS

| | | | | |
|---|---|---|---|---|
| 2,116,328 A | * | 5/1938 | Silten | ............ 128/203.16 |
| 3,912,795 A | * | 10/1975 | Jackson | ............ 261/36.1 |
| 4,038,980 A | | 8/1977 | Fodor | |
| 4,090,513 A | * | 5/1978 | Togawa | ............ 128/201.13 |
| 4,146,597 A | | 3/1979 | Eckstein | |
| 4,319,566 A | | 3/1982 | Hayward et al. | |

(Continued)

FOREIGN PATENT DOCUMENTS

BE 1003559 A4 4/1992

(Continued)

OTHER PUBLICATIONS

MR410 Respiratory Humidifier, Fisher & Paykel Healthcare Brochure 1995.

(Continued)

*Primary Examiner*—Justine R Yu
*Assistant Examiner*—Clinton Ostrup
(74) *Attorney, Agent, or Firm*—Procopio, Cory, Hargreaves & Savitch LLP

(57) ABSTRACT

A humidifier system for heating and humidifying respiratory gases has a housing with an inner chamber, a first port at the first end for connection to a ventilator breathing circuit and a second port at the second end for connection to a patient to supply respiratory gases to the patient and to receive exhaled gases from the patient. A body of heat moisture exchange (HME) material is located within the chamber, and a water permeable device is also located within the chamber. The housing has a water refill inlet communicating with the water permeable device. A water supply outside the housing is connected to the water refill inlet to supply water to the water permeable device. A heater mounted outside the housing supplies heat to the housing and maintains the housing at a selected temperature.

20 Claims, 5 Drawing Sheets

U.S. PATENT DOCUMENTS

| | | | | |
|---|---|---|---|---|
| 4,500,430 | A * | 2/1985 | Dasgupta | 210/638 |
| 4,621,633 | A | 11/1986 | Bowles et al. | |
| 4,652,408 | A * | 3/1987 | Montgomery | 261/130 |
| 4,773,410 | A | 9/1988 | Blackmer et al. | |
| 4,825,863 | A | 5/1989 | Dittmar et al. | |
| 4,948,435 | A * | 8/1990 | Butler et al. | 148/529 |
| 4,972,759 | A * | 11/1990 | Nelson | 122/494 |
| 5,062,145 | A | 10/1991 | Zwaan | |
| 5,109,471 | A | 4/1992 | Lang | |
| 5,116,088 | A | 5/1992 | Bird | |
| 5,172,686 | A | 12/1992 | Anthony | |
| 5,320,096 | A * | 6/1994 | Hans | 128/205.29 |
| 5,349,946 | A * | 9/1994 | McComb | 128/203.17 |
| 5,383,447 | A | 1/1995 | Lang | |
| 5,434,387 | A * | 7/1995 | Haley | 219/535 |
| 5,435,298 | A | 7/1995 | Anthony | |
| 5,462,048 | A | 10/1995 | Lambert et al. | |
| 5,640,951 | A * | 6/1997 | Huddart et al. | 128/204.17 |
| 5,647,344 | A * | 7/1997 | Turnbull | 128/201.13 |
| 5,701,891 | A * | 12/1997 | Groenke | 128/205.29 |
| 5,714,738 | A * | 2/1998 | Hauschulz et al. | 219/535 |
| 5,769,071 | A | 6/1998 | Turnbull | |
| 5,906,201 | A | 5/1999 | Nilson | |
| 5,988,164 | A | 11/1999 | Paluch | |
| 5,992,413 | A | 11/1999 | Martin, Jr. et al. | |
| 6,102,037 | A | 8/2000 | Koch | |
| 6,363,930 | B1 | 4/2002 | Clawson | |
| 6,367,472 | B1 | 4/2002 | Koch | |
| 6,474,335 | B1 | 11/2002 | Lammers | |
| 6,550,476 | B1 * | 4/2003 | Ryder | 128/201.13 |
| 6,557,551 | B2 | 5/2003 | Nitta | |
| 6,769,431 | B2 * | 8/2004 | Smith et al. | 128/203.16 |
| 6,779,522 | B2 * | 8/2004 | Smith et al. | 128/203.16 |
| 6,976,489 | B2 * | 12/2005 | Mantell et al. | 128/204.17 |
| 7,120,354 | B2 | 10/2006 | Mackie | |
| 2004/0074493 | A1 | 4/2004 | Seakins et al. | |
| 2004/0118225 | A1 * | 6/2004 | Wright et al. | 73/866 |
| 2005/0166915 | A1 | 8/2005 | Gibertoni | |
| 2006/0012057 | A1 | 1/2006 | Anthony | |
| 2006/0081247 | A1 | 4/2006 | Britt | |
| 2006/0162726 | A1 | 7/2006 | Smith | |

FOREIGN PATENT DOCUMENTS

| | | |
|---|---|---|
| DE | 196 02 077 A1 | 8/1996 |
| EP | 0 567 158 A2 | 10/1993 |
| EP | 0 754 470 A2 | 6/1996 |
| GB | 2 277 689 | 11/1994 |

OTHER PUBLICATIONS

900MR748 Adult Breathing Circuit Kit, Fisher & Paykel Healthcare, date unknown.

Humidification and Filtration Products, tkb Surgical Products brochure, 2001.

Medisize HME Booster, http://www.hmebooster.com (earliest publication date unknown).

* cited by examiner

HUMIDIFIER SYSTEM FOR ARTIFICIAL RESPIRATION

BACKGROUND OF THE INVENTION

The present invention relates to a humidifier system for humidifying and warming respiratory gases for patients requiring artificial respiratory support.

When a person breathes normally, the mucous membrane of his upper airway can heat and humidify the inspired gases to the body temperature (37° C.) and 100% relative humidity before the gases enter the lung. When a patient is under mechanical ventilation, his upper airway is bypassed due to the artificial airway (such as an endotracheal tube or tracheostomy). Because the gases from mechanical ventilators usually are cold and dry, the patient needs to have the inspired gases heated and humidified before the gases enter into his lung in order not to lose the body heat and water.

Traditionally, there are two techniques to help the patient to achieve the goals of heating and humidifying inspiratory gases from a mechanical ventilator. One of them is to use a device called an active heated humidifier. One example of this device is the heated humidifier developed and manufactured by Fisher & Paykel, a New Zealand based company. This device compromises a heater, a water chamber that is heated by the heater, and sometimes a heated wire that is placed in the breathing circuit of a mechanical ventilator. The cold and dry gases that come from the mechanical ventilator will first flow through the water chamber before entering the patient lung, and will be heated and humidified by touching the hot water in the water chamber. In some cases, a heated wire is placed in the breathing circuit to maintain a stable high temperature in order to avoid water condensation in the long breathing circuit.

The other traditional technique is to use a passive heat moisture exchanger or hygroscopic condenser humidifier (HME). One such HME is made by Hudson RCI Inc. (Temecula, Calif.). This HME is made of a plastic housing and HME material that is placed inside of the housing. The HME material is usually made of hygroscopic foam or paper that may also be treated with salts. When the HME is placed at the out end of the artificial airway, it will retain the heat and moisture from the exhaled gases when the patient exhales. In the next inspiration, the dry and cold gases from the mechanical ventilator will be heated and humidified by the heat and moisture that were retained in the HME in the previous breath.

Active heated humidifiers provide good heating and humidifying capability from the patient physiological point of view. However, it is very cumbersome to use such humidifiers, requiring assembly of the breathing circuit in a special way. It also has poor power efficiency because the heat is wasted through the breathing circuit which is in heat exchange with the room air. The use of heated wire in the breathing circuit may also impose an electrical and fire safety concern. Passive HME, on the other hand, is very convenient for use and does not impose any safety concern from an electrical and fire standpoint. The limitation of HME is its inadequate heating and humidifying power. While the inspired gases need to contain moisture at 44 mg/L in order to get 100% relative humidity at 37° C., a HME usually can only provide 30 mg/L. Therefore, HME is not able to be used in long-term mechanical ventilation due to its inadequate capability.

In order to avoid the shortcomings of the active heated humidifier and the passive HME, some inventors have conceived designs that combine a passive HME with active heating and humidifying elements. Some combined HME and active heated humidifiers are very complicated and have numerous parts, resulting in a high cost. This means that they cannot be used in a disposable manner, and re-use produces a risk of cross infection.

In some combination designs, a HME material, a heating element, and a water evaporating element are all enclosed within a housing. The water evaporating element is connected to the outside water tube to refill water. The heating element is connected to the outside electrical power. All these designs have a risk of electrical and fire hazard. If the heating element is overheated as the result of control error or as the result of empty water tubing, the heating element in the housing may burn the materials that are in the housing. This is risky, especially if the patient is using a high concentration of oxygen.

SUMMARY OF THE INVENTION

It is an object of the present invention to provide a new and improved humidifier system to humidify and warm the gases provided to patients undergoing artificial respiration.

According to one aspect of the present invention, a humidifier apparatus for heating and humidifying respiratory gases is provided, which comprises a housing having an inner chamber with an inlet for connection to a ventilator output and an outlet for connection to a patient to supply respiratory gases to the patient, the chamber containing a heat moisture exchange (HME) material and a water permeable element, the housing having a water refill inlet communicating with the water permeable element, a water supply outside the housing connected to the water refill inlet to supply water to the water permeable element, and a heating element outside the housing for heating the housing and maintaining the housing at a predetermined temperature.

In an exemplary embodiment of the invention, the heating element is releasably mounted around the housing, and may be of a clamshell design, having two semi-cylindrical halves joined together by a hinge along one longitudinal edge. The two halves can be closed together around the outside of the housing, with the free longitudinal edges secured together by a releasable latch. With this arrangement, the heating element is re-usable since it is completely outside the housing and not exposed to any potential contaminants within the housing, while the housing and contents may be disposed of and replaced after each use.

The moisture and heat exchange (HME) material may be of paper or hygroscopic material, and may be pre-treated with salts, such as calcium chloride. This material is used to retain the heat and moisture from the patient's exhaled gases during the exhalation part of the breathing cycle. The retained heat and moisture will be picked up by the incoming cold and dry gases from the ventilator during the next inspiratory phase. The heating element helps to reduce loss of heat from the moisture and heat retaining material.

In one example of the invention, the housing is elongate and has a body of moisture and heat retaining material extending along its length, while the water permeable element comprises a wire or elongate member which is wound around the moisture and heat retaining material in a spiral manner along at least part of the length of the body. The wire may comprise a bundle of porous fibers or a bundle of tubes which can transport water and which have walls which are water permeable. The walls may be of a material which transports water across the membrane or wall by chemical reaction, such as Nafion®. The fibers or tubes are connected to the water supply or refill system outside the housing. When the dry, incoming gases pass through or alongside the water permeable wire, they will take the water out of the wire through the water permeable membrane or walls of the tubes. The water refill system will then automatically refill the tubes through gravity.

Although the water permeable element is an elongate or wire-like member in the exemplary embodiment, it may be of other shapes and may be a planar member with internal hollows or cavities. The heat and moisture retaining (HME) material may be any type of material which is typically used in a passive heat moisture exchanger (HME) or hygroscopic condenser humidifier, such as hygroscopic foam, paper treated with a salt such as calcium or lithium salts, or other heat and moisture exchange material. The water permeable element may extend the entire length of the chamber, along with the heat and moisture retaining material, or may extend only part of the length of the housing up to the outlet, leaving a portion of the housing on the ventilator or inlet side containing heat and moisture exchange material only. The water permeable element or wires may extend beyond the end of the heat and moisture retaining material at the patient end of the housing.

The heating element may be controlled to heat the housing to a predetermined temperature, which may be a fixed temperature or may be adjustable by the user. In an exemplary embodiment of the invention, a control temperature sensor or thermometer is placed on the outer surface of the housing for monitoring the temperature. The control thermometer has an output connected to a control system for adjusting the heater power output based on the desired temperature level. A second thermometer spaced from the control thermometer may be used for monitoring the actual temperature and an output display of the monitored temperature may be provided.

The humidifier system of this invention combines a passive heat moisture exchanger and an active heated humidifier or water permeable element combined together in a single chamber within a housing, with a heating element placed outside the housing. The water permeable element will actively add humidity to the respiratory gases through its water permeable membrane, while the respiratory gases will take up water and heat from the passive HME body. By placing the heating element outside the housing, rather than inside, the risks of overheating, fire, and electrical hazards are reduced. The temperature control system will avoid overheating, which could potentially cause airway burning, and under heating, which could cause hypothermia. Because the heating element is outside the housing, not inside the housing where cross infection or contamination is a concern, the heating element can be made as a reusable part. The only disposable parts are the housing and its contents, making the device inexpensive for single use.

The water permeable element comprises a wire or elongate member wound around the heat moisture exchanger element, reducing the amount of dead space in the humidifier housing. This reduces the amount of carbon dioxide in the exhaled gases remaining in the humidifier to be re-inhaled by the patient, reducing the risk of hypercarbonate and acidosis in the patient's blood.

This arrangement provides a combined active humidifying element with a passive HME body in a single, compact housing which can be made inexpensively as a disposable unit for single patient use. At the same time, the heater is outside the housing and can be re-used to save cost, since it is not exposed to potential cross-infection or contamination.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

DETAILED DESCRIPTION OF THE DRAWINGS

Figure 1:
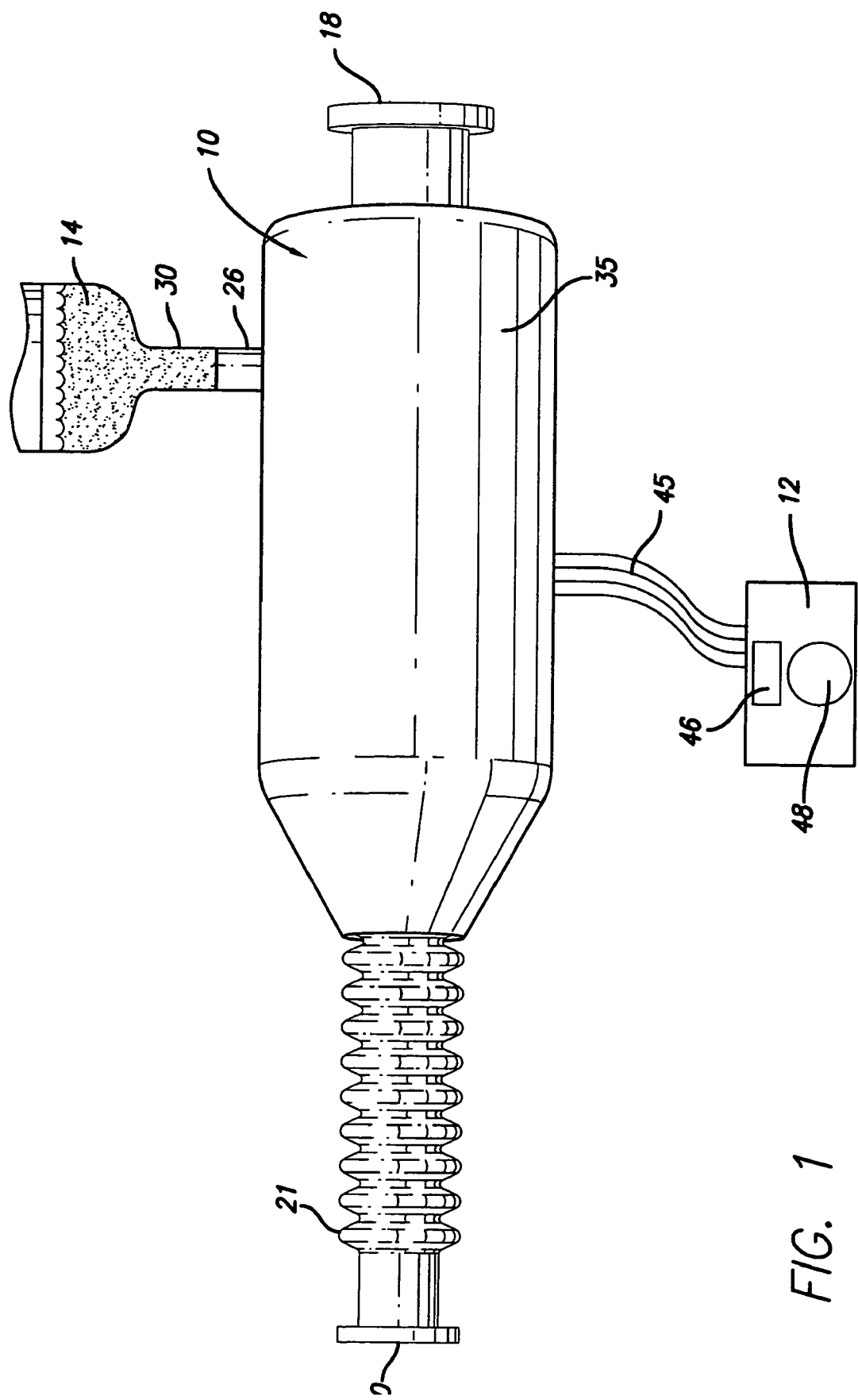
FIG. 1 is a schematic illustration of the humidifier system according to an exemplary embodiment of the invention.

FIG. 1 illustrates a humidifier system according to an exemplary embodiment of the invention, while FIGS. 2 to 5 illustrate details of the humidifier device 10 of FIG. 1. The system basically comprises humidifier device 10 which is adapted to be connected in-line between a ventilator and a patient, a temperature control and power supply unit 12 connected to the humidifier device, and a water supply unit 14 having a water refill line 30 also connected to the humidifier device.

Figure 2:
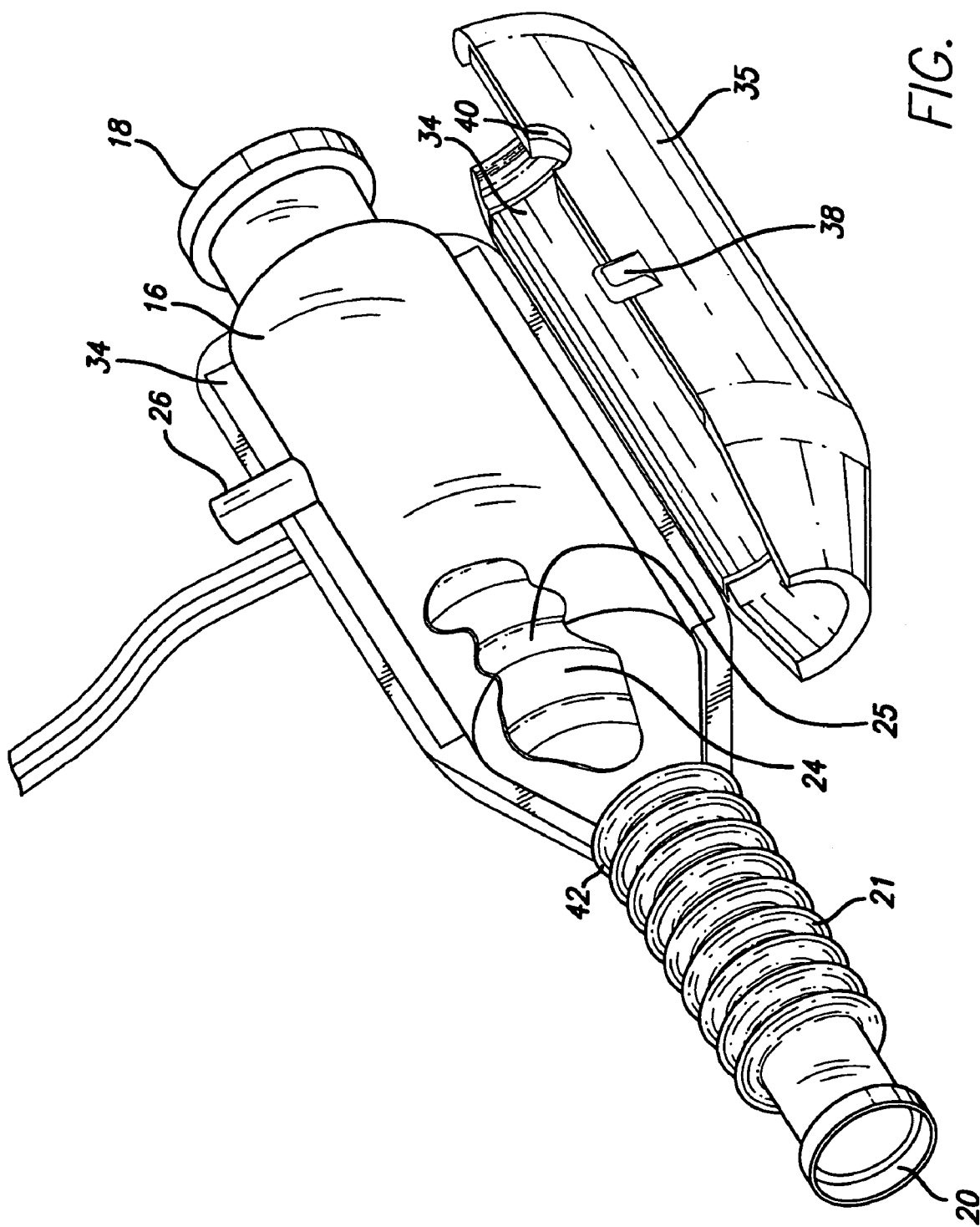
FIG. 2 is a perspective view, partially broken away, of the humidifier device with the external heater in the open position.
Figure 3:
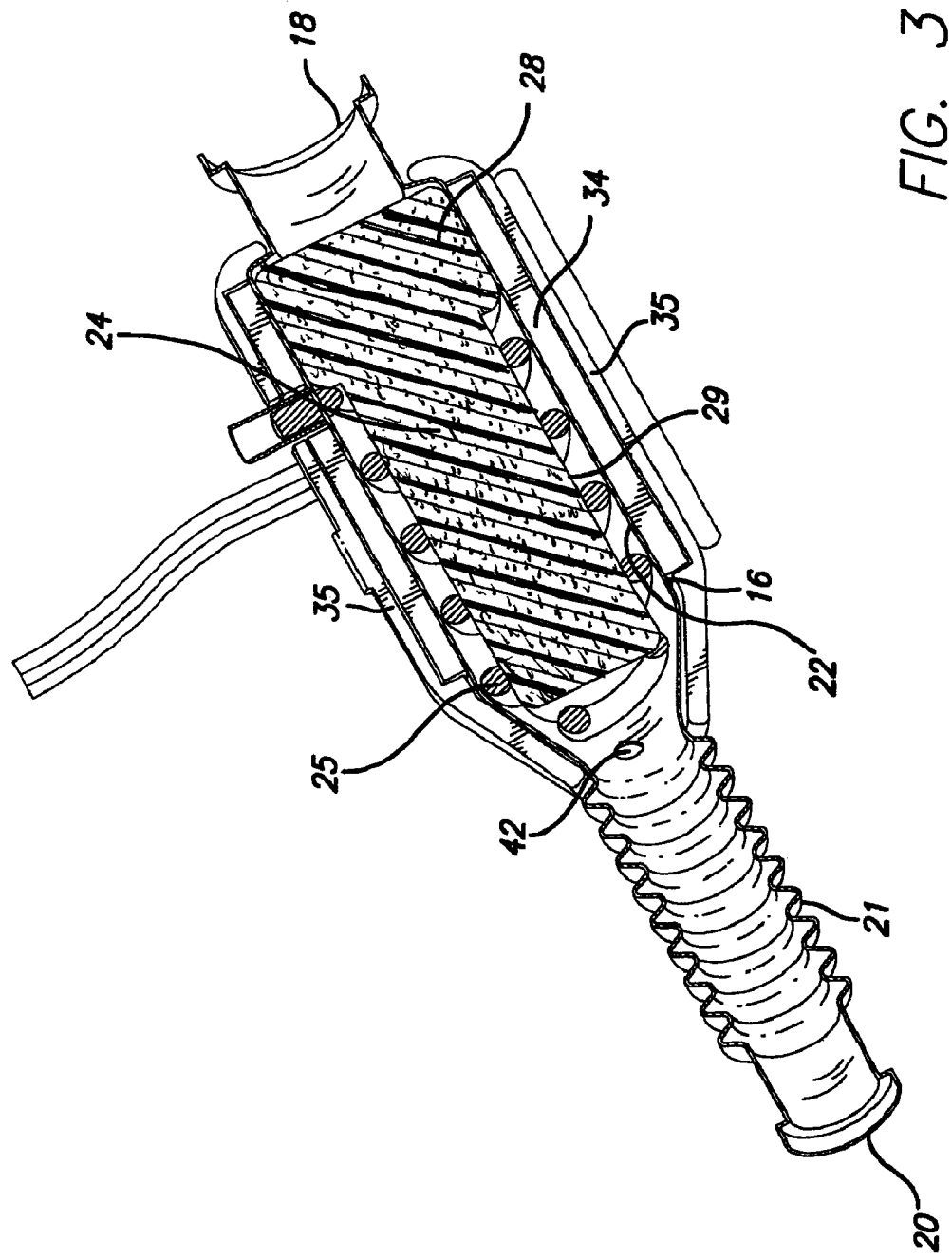
FIG. 3 is a horizontal cross-sectional view of the humidifier device.

The humidifier device is illustrated in more detail in FIGS. 2 and 3 and comprises an elongate housing 16 having a connector port 18 at one end for connection to a ventilator breathing circuit and a second connector port 20 at the opposite end for connection to a patient. The housing may be of plastic or thermoconductive plastic. A length of flexible tubing 21 connects port 20 to the housing, for reducing tension between the humidifier system and the patient when the patient moves his or her head or when the medical staff is conducting airway care. A humidifier chamber 22 in the housing contains a body 24 of heat and moisture exchange (HME) material and an elongate, wire-like water permeable member 25 is wound around the outside of body 24 in a spiral manner, as best illustrated in FIGS. 2 and 3. One end of the member 25 extends into a connector port 26 on the housing for connection to the water refill line 30.

As best illustrated in FIG. 3, the HME material body 24 has a larger diameter portion 28 adjacent the first connector port 18, which substantially fills the humidifier chamber 22, and a smaller diameter portion 29 extending from portion 28 up to the end of the chamber 22. The water permeable member or wire 25 is wound around the smaller diameter portion 29 from the port 26, which is adjacent the junction between the smaller and larger diameter portions of the HME body, and up to the end of portion 29. The water permeable member in this embodiment extends along approximately two-thirds of the length of chamber 22 up to the patient end of the chamber. This leaves one-third of the length of the chamber on the respirator side filled with HME material only. The water permeable member or wire may extend beyond the end of body 24, as indicated in FIG. 2. One end of the wire 25 is connected to the water supply 14 via water refill line 30 at the connector port 26.

Figure 4:
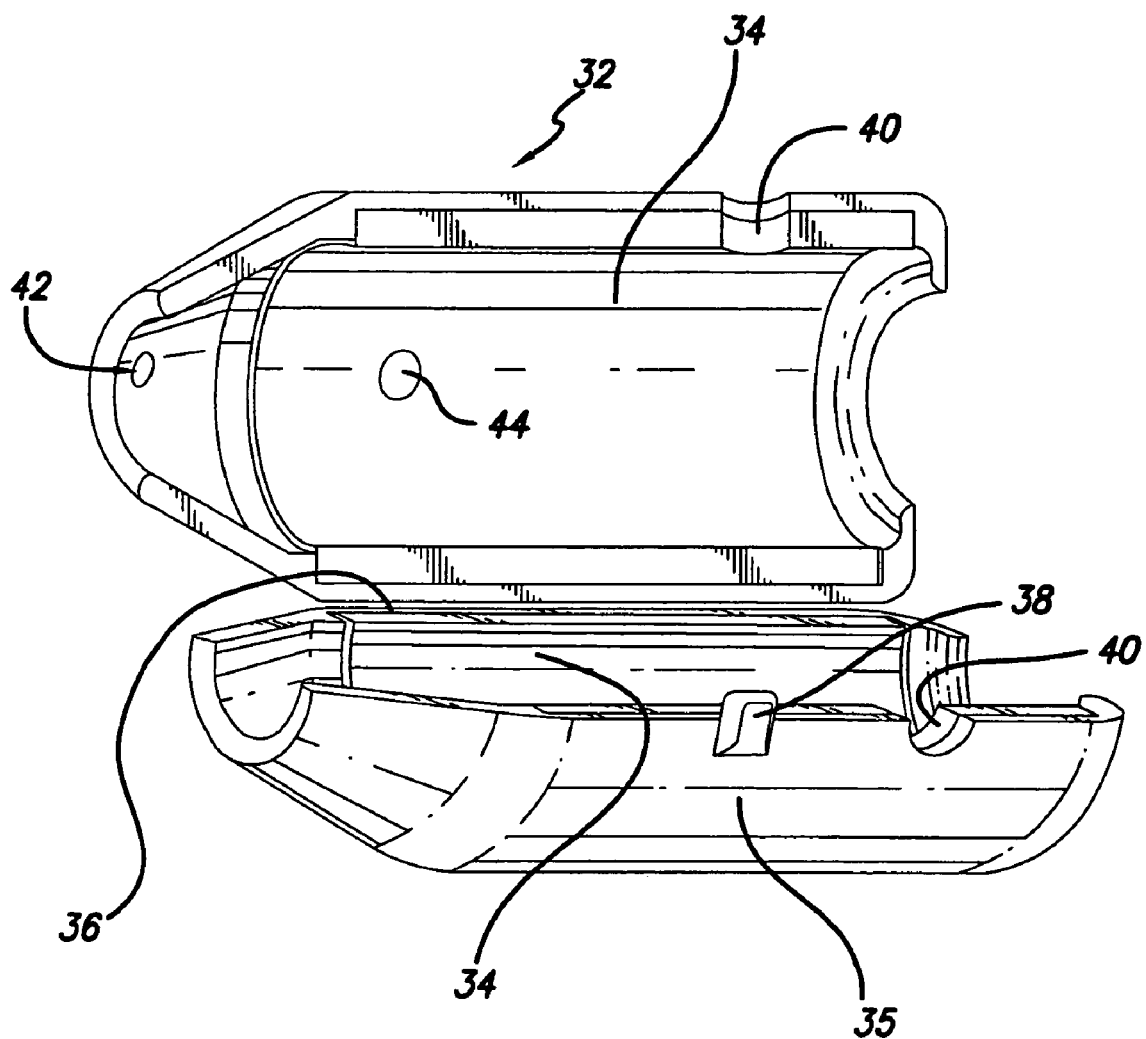
FIG. 4 is a perspective view of the external heater separated from the humidifier housing, with the heater in the open position.

A heater 32 of a clamshell design is releasably secured around the housing so as to completely surround the housing and extend the full length of the humidifier chamber 22, as best illustrated in FIGS. 2 to 4. Since the heater is outside and separate from the housing 16, there will be no electrical current within the housing. The heater 32 is shown separated from the humidifier housing in FIG. 4. The heater 32 has a two part, cylindrical heating element 34 and an outer heat insulating cover 35. Heat insulating cover 35 protects and surrounds the heating element 34 in order to reduce heat loss to the surrounding room air and to prevent burning of the patient or medical personnel.

The heating element may be an electrical heating element, microwave heater, or any other type of heat generator. The heating element and outer cover are formed as two semi-cylindrical halves joined together by a hinge 36 along one longitudinal edge. The hinge may be a physical hinge or may be a functional hinge formed by a thinner portion of the heating element and/or cover material. The two halves of the heater can be closed together around the outside of the housing, with the free longitudinal edges secured together by a releasable latch 38 which may be of any conventional design. The opposite longitudinal edges of the outer casing and heater element halves have matching notches or indents 40 for fitting around the water inlet or connector port 26.

The heating element 34 terminates short of a first end of the insulating cover 35 on the patient side of the humidifier, as illustrated in FIG. 2. A first temperature sensor or thermometer 42 is mounted on the inner surface of the outer cover or casing 35 of the heater adjacent the first end, at a location spaced from the heating element 34, as best illustrated in FIGS. 3 and 4. The sensor is positioned such that it will contact the outer surface of the housing 16 when the heater is secured around the housing and will monitor the downstream housing temperature. One or more additional temperature sensors 44 may be placed on the inner surface of the heating element 34 upstream of the first temperature sensor to monitor the heater. The sensor or sensors are used to monitor temperature and provide feedback to the temperature control system of unit 12.

Cables 45 connect the heater and the temperature sensors to the control unit 12 which controls power supply to the heater elements and monitors the temperature. A display 46 indicates the actual temperature detected by the temperature sensor 42 (monitor thermometer). A control knob 48 is provided on unit 12 for a user to modify the temperature setting. The control unit 12 is also arranged to control the power output to the heater in a real time manner based on the temperature detected by sensors 42 and 44 in order to achieve the user-selected housing temperature. If the actual temperature detected is too high, the power supply will be controlled to reduce the heater power output. If the temperature becomes too low, the power supply to the heater will be increased until the desired temperature is achieved. This arrangement provides active servo control of the temperature in housing 16, which provides a more constant temperature. This reduces the risk of overheating and potential airway burning, or underheating which may result in hypothermia.

The HME material may be paper, foam, or any other material that can retain moisture and heat. The body of HME material will be sufficiently porous to allow gas flow through the material, so that moisture and heat can be taken up from the material into the inhaled respiratory gases, and the material can absorb heat and moisture from gases exhaled by the patient.

Figure 5:
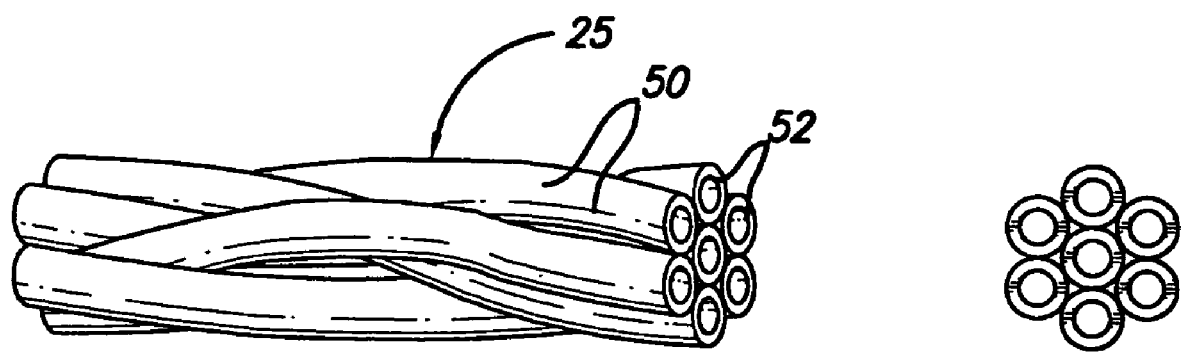
FIG. 5 is a perspective view of a portion of a water permeable wire forming part of the humidifier.

The elongate water permeable element or wire 25 is made of water permeable material, and may comprise a bunch of multiple fibers with hollows inside, such as STERAPORE® hollow fiber made by Mitsubishi Rayon Co. Ltd of Japan. Alternatively, as illustrated in FIG. 5, the water permeable element 25 may comprise a plurality of hollow tubes 50 having walls 52 made of a water permeable membrane. The tubes are braided together as indicated in FIG. 5 to form a wire or single elongate member 25 which can be wound around the inner wall of the chamber 22 or around the outside of HME element 24. The tubes 50 may be any type of water transportable tube such as Nafion® tubes made by PermaPure LLP of Toms River, N.J. Nafion® tubes transport water across the membrane or tube wall through chemical reaction of the water with the Nafion® material. The tubes 50 will be filled with water from the water supply 14 under the action of gravity. The automatic refilling of the tubes with water by gravity can avoid over hydration which can happen with an active water refill system. An optional water drop sensor may be provided in the water refill line 30 in order to detect an empty water refill line and provide an alert to the system operator that the water bottle or supply 14 needs to be replaced or refilled.

Although the water permeable element is wound around the outside of the body of HME material in the illustrated embodiment, between the HME material and the inner wall of the housing, it may be positioned differently in alternative embodiments. For example, it may be located in the space between the patient end of the body of HME material and the connector 20 to the patient.

When the humidifier system of this invention is assembled as in FIG. 1 and connected in line between a ventilator breathing circuit and a patient, and the patient inhales, cold and dry gases coming from the ventilator will enter the humidifier chamber 22 via port 18, and then enter the patient respiratory system via connector port 20. The cold and dry gases entering chamber 22 will first retake heat and moisture retained in the HME material 24. They will be further heated by the heater 32 that is attached to and surrounds the housing 16. The dry gases passing through the moisture permeable tubes 50 will also take up water through the permeable membrane, and the water refill system will refill the water into the tubes automatically through gravity. Thus, the ventilator gases will be heated and humidified before they reach the patient's lungs.

When the patient exhales, the exhaled gases will enter the humidifier chamber via connector port 20, pass across the water permeable wires or tubes 50 and through the HME element, and then exit via port 18 to the room air through the expiratory limb of the ventilator breathing circuit. The heat and moisture in the exhaled gases will be retained in the heat moisture exchanger material 24, and will then be retaken by the incoming cold and dry gases from the ventilator in the next inhalation.

The humidifier system may also have an optional gas sampling port at a suitable location for connection to a respiratory gas monitor to monitor the gas concentrations in the patient inspired or exhaled gases.

The humidifier housing and contents, ports 18, 20, and flexible tubing 21 can be made as a single use unit, with all other components being reusable. This is feasible because of the removable mounting of the heater 32 outside of the housing and completely out of contact with the patient exhaled gases. The water bottle and water refill bottle can also be reused if the permeable membrane of the water permeable wires or tubes 50 does not permit microorganisms to pass through the membrane. An example of a suitable membrane material which does not permit passage of microorganisms is Nafion®. Because the only disposable parts in this system are the HME element, water permeable wires, and housing (which may be of plastic material), the humidifier device can be made inexpensively. Placement of the heater element completely outside the housing reduces the risk of overheating and fire hazard, and also eliminates the risk of contamination or cross-contamination of the heater components by respiratory gases.

The positioning of the water permeable element in the same chamber as the HME material will reduce the dead space in the humidifier where carbon dioxide may collect, thereby reducing carbon dioxide re-breathing by the patient. This in turn will reduce the risk of hypercarbonate and acidosis in the patient's blood. By forming a water permeable element of multiple tiny hollow tubes which are braided together, as indicated in FIG. 5, the contact area between the water permeable element and the respiratory gases will be increased over a water permeable element which comprises a simple flat membrane or the like.

Heat moisture exchanger materials, or materials that can retain moisture and heat and give up the retained moisture and heat to gases passing through them, perform most efficiently if the temperature is maintained at a high level. The external heater in the humidifier of this invention is controlled to maintain the optimum temperature in the housing and to reduce the risk of over or under heating.

Although an exemplary embodiment of the invention has been described above by way of example only, it will be understood by those skilled in the field that modifications may be made to the disclosed embodiment without departing from the scope of the invention, which is defined by the appended claims.

We claim:

1. A humidifier system for heating and humidifying respiratory gases, comprising:
    a housing having opposite first and second ends and a chamber between said ends defining a flow path for respiratory gases, a first port at the first end for connection to a ventilator breathing circuit and a second port at the second end for connection to a patient to supply respiratory gases to the patient and to receive exhaled gases from the patient;
    a body of heat moisture exchange (HME) material within the chamber, the HME material comprising a material which can retain moisture and heat;
    a water permeable device of a water permeable material different from said HME material, the water permeable device located within the chamber and extending along at least part of the length of the body of HME material, the housing having a water refill inlet communicating with the water permeable device;
    a water supply outside the housing connected to the water refill inlet to supply water to the water permeable device; and
    a heater mounted outside the housing for heating the housing and maintaining the housing at a predetermined temperature; wherein the water permeable device is elongate and is wound around the moisture and heat retaining material in a spiral manner along at least part of the length of the HME material body, whereby respiratory gasses contact the water permeable device.

2. The system as claimed in claim 1, wherein the heater is releasably mounted around the housing.

3. The system as claimed in claim 2, wherein the heater is of cylindrical shape and predetermined dimensions for fitting closely around the housing and comprises first and second semi-cylindrical halves having first and second pairs of mating longitudinal edges, said halves being hinged together along one pair of longitudinal edges and having a releasable latch mechanism on the second pair of longitudinal edges for releasably securing the halves together in a closed position around the housing.

4. The system as claimed in claim 3, wherein each half of the heater comprises a semi-cylindrical, continuous heating element and an outer insulating cover extending over the heating element.

5. The system as claimed in claim 4, wherein the insulating cover is longer than the heating elements and each heating element has an end closest to the second end of the housing which terminates short of the corresponding end of the insulating cover to leave a projecting end portion of the cover, and a temperature sensor is mounted on an inner face of the projecting end portion of the insulating cover, whereby the temperature sensor will contact the outer surface of the housing when the heater is in the closed position around the housing, and a control unit is connected to said temperature sensor and heater for controlling the heater output to maintain the housing at a selected temperature.

6. The system as claimed in claim 5, including an additional temperature sensor spaced from the first temperature sensor on the inner surface of the heating element, the additional temperature sensor being connected to said control unit, and both temperature sensor outputs being used to monitor housing temperature and control heater output.

7. The system as claimed in claim 1, wherein the water supply is located above the housing for supplying water to the water permeable device by gravity.

8. The system as claimed in claim 1, including at least one temperature sensor which detects the temperature of the housing, and a control unit connected to said temperature sensor and heater for controlling the heater output to maintain the housing at a selected temperature.

9. The system as claimed in claim 8, wherein the housing has an outer surface and an inner surface, and the temperature sensor is mounted against the outer surface of the housing.

10. The system as claimed in claim 9, wherein the temperature sensor is mounted on an inner wall of the heater, whereby the sensor contacts the outer surface of the housing.

11. The system as claimed in claim 1, wherein the HME material body extends along at least a major portion of the length of the chamber from the first end, and the water permeable device extends along part of the length of the HME material body up to the second end of the housing.

12. The system as claimed in claim 1, wherein the water permeable element extends beyond the end of the HME material body at the patient end of the housing.

13. A humidifier system for heating and humidifying respiratory gases, comprising:
    an elongate housing having opposite first and second ends and a chamber between said ends defining a flow path for respiratory gases, a first port at the first end for connection to a ventilator breathing circuit and a second port at the second end for connection to a patient to supply respiratory gases to the patient and to receive exhaled gases from the patient;
    a body of heat moisture exchange (HME) material within the chamber, the HME material comprising a material which can retain moisture and heat;
    a water permeable device within the chamber, the housing having a water refill inlet communicating with the water permeable device;
    a water supply outside the housing connected to the water refill inlet to supply water to the water permeable device;
    a heater mounted outside the housing for heating the housing and maintaining the housing at a predetermined temperature; and
    the body of HME material extending along at least a major part of the length of the chamber and substantially filling the chamber, whereby respiratory gases flowing through the chamber contact the material; wherein the water permeable device is elongate and is wound around the moisture and heat retaining material in a spiral manner along at least part of the length of the HME material body, whereby respiratory gasses contact the water permeable device.

14. The system as claimed in claim 13, wherein the water permeable device comprises a plurality of tubes which are wound together to form an elongate braided member, each tube having a wall which is water permeable.

15. The system as claimed in claim 14, wherein each tube wall is of a material which transports water across the wall by chemical reaction.

16. A humidifier apparatus, comprising:
a housing having opposite first and second ends, a first port at the first end of the housing and a second port at the second end of the housing, and a chamber in the housing communicating with said first and second ports;
a heat moisture exchange (HME) material within the chamber for contact with respiratory gases flowing though the chamber between said ports;
a water permeable device within the chamber for adding humidity to respiratory gases, the water permeable device being of a water permeable material which is different from said HME material, at least part of the water permeable device being located in the same region of the chamber as the HME material;
the housing having a water supply port connected to said water permeable device for supplying water from an external water supply to refill said water permeable device; and
a heater mounted outside the housing and surrounding the chamber; wherein the water permeable device is elongate and is wound around the moisture and heat retaining material in a spiral manner along at least part of the length of the HME material body, whereby respiratory gasses contact the water permeable device.

17. The apparatus as claimed in claim 16, wherein the heater is removably mounted around the housing.

18. The apparatus as claimed in claim 16, including a temperature sensor for detecting the temperature of the housing, and a control unit connected to the heater and the temperature sensor for controlling the heater to heat the housing to a predetermined temperature.

19. A humidifier apparatus, comprising:
a housing having opposite first and second ends, a first port at the first end of the housing and a second port at the second end of the housing, and a chamber in the housing communicating with said first and second ports;
a body of heat moisture exchange (HME) material within the chamber for contact with respiratory gases flowing though the chamber between said ports;
a water permeable device within the chamber for adding humidity to respiratory gases, at least part of the water permeable device being located in the same region of the chamber as the HME material;
the housing having a water supply port connected to said water permeable device for supplying water from an external water supply to refill said water permeable device;
a heater mounted outside the housing and surrounding the chamber; and
the body of heat moisture exchange material comprising a generally is elongate and is wound around the moisture and heat retaining material in a spiral manner along at least part of the length of the HME material body, whereby respiratory gasses contact the water permeable device.

20. The apparatus as claimed in claim 19, wherein the elongate member comprises a plurality of hollow tubes wound together, each tube having a wall made of water permeable material.

* * * * *